United States Patent [19]
Goldberger et al.

[11] Patent Number: 5,387,122
[45] Date of Patent: Feb. 7, 1995

[54] PULSE OXIMETER PROBE CONNECTOR

[75] Inventors: Daniel S. Goldberger, Boulder; Timothy A. Turley, Highlands Ranch; Kirk L. Weimer, Louisville, all of Colo.

[73] Assignee: Ohmeda Inc., Liberty Corner, N.J.

[21] Appl. No.: 63,398

[22] Filed: May 18, 1993

Related U.S. Application Data

[63] Continuation-in-part of Ser. No. 781,891, Oct. 24, 1991, Pat. No. 5,249,576.

[51] Int. Cl.⁶ .......................................... H01R 13/627
[52] U.S. Cl. ................................. 439/353; 439/374; 439/909
[58] Field of Search ............... 439/352, 353, 354, 357, 439/374, 378, 909

[56] References Cited

U.S. PATENT DOCUMENTS

| | | | |
|---|---|---|---|
| 4,842,543 | 6/1989 | Davis | 439/378 |
| 5,069,634 | 12/1991 | Chiarolanzio | 439/353 |
| 5,080,603 | 1/1992 | Mouissie | 439/353 |
| 5,092,788 | 3/1992 | Pristupa, Jr. et al. | 439/352 X |
| 5,127,844 | 7/1992 | Léman et al. | 439/374 X |
| 5,252,089 | 10/1993 | Hatagishi et al. | 439/378 X |

OTHER PUBLICATIONS

IBM Technical Disclosure Bulletin, vol. 34, No. 2, Jul. 1991.

*Primary Examiner*—Khiem Nguyen
*Attorney, Agent, or Firm*—Roger M. Rathbun; Larry R. Cassett; James M. Graziano

[57] ABSTRACT

The pulse oximeter probe uses an inexpensive connector to electrically interconnect the sensor elements with the pulse oximeter. One segment of the probe connector contains a set of connector pins that are wired to the sensor elements. Another segment of the probe connector is equipped with a mating configuration of sockets which align with these pins. Three projections function to automatically align the connector pins with the connector sockets. Two of the projections engage a mating aperture in the other connector segment to fasten the two connector segments together, while a third projection aligns with an edge of the other connector segment to position the two connector segments.

12 Claims, 7 Drawing Sheets

PULSE OXIMETER PROBE CONNECTOR

CROSS-REFERENCE TO RELATED APPLICATIONS

This application is a continuation-in-part of U.S. patent application Ser. No. 07/781,891, titled Universal Pulse Oximeter Probe, filed on Oct. 24, 1991 now U.S. Pat. No. 5,249,576, Oct. 5, 1993.

FIELD OF THE INVENTION

This invention relates to medical monitoring equipment and, in particular, to an inexpensive universal probe, containing disposable sensor elements, that interfaces to a plurality of different pulse oximeter instruments.

PROBLEM

It is a problem in the field of monitoring equipment in biomedical technology to produce a probe, including sensor elements, that is inexpensive, simple to use, accurate in their measurements and yet disposable. In the field of pulse oximetry, the pulse oximeter instrument is connected to a subject via a disposable probe, which is connectorized to be detachable from the pulse oximeter instrument. The probe includes a sensor circuit that consists of a pair of light emitting diodes and a photodetector that are incorporated into a housing that can be applied to the subject in order to measure the oxygenation of the subject's blood. Present pulse oximeter probes use a connectorized long cable, hard-wired at one end to the light emitting diodes and light detector. The housing can be of many configurations due to the fact that the pulse oximeter instrument is used with adult subjects, children and infants. Each of these classes of subjects may require a different means of attaching the active sensor elements to a blood carrying member of the subject. For example, the sensors can be attached to the subject's finger, ear, foot or septum, each of which application requires a different housing for the sensors. Another complicating factor is that each pulse oximeter instrument utilizes a different connector configuration and possibly a different sensor element wiring configuration in the probe.

It is obvious that a hospital must stock a large diversity of pulse oximeter probes, each of which is a disposable element. The proliferation of probe types produces an inventory problem as well as increased cost to the patient, since a significant segment of the manufacturing costs of the probe is the connector and associated wiring that interconnects the sensor elements to the pulse oximeter instrument. The manufacturers of pulse oximeter probes also do not have the economies of scale of making a single probe, but instead must manufacture numerous different incompatible probes.

SOLUTION

The above described problems are solved and a technical advance achieved in the field by the pulse oximeter probe connector of the present invention which utilizes an inexpensive probe connector configuration to enable the connector/cable section of the probe to be used numerous times. The probe connector is both mechanically simple and electrically reliable and functions to interconnect the housing containing the sensor elements with the cable that connects the pulse oximeter instrument to the sensor elements. This probe connector enables the user to obtain significant benefits due to the fact that the expensive cable segment of the probe is a separable element from the housing segment of the probe that contains the sensor elements.

In particular, the cable segment of the probe consists of a monitor connector that is compatible with the pulse oximeter instrument and which is terminated at the other end in the probe connector of the present invention. The probe housing contains the mating other half of this probe connector, the sensor elements and a means of mechanically affixing the sensor elements to the subject. Thus, the cable segment of the probe is reusable numerous times and the disposable part of the probe consists only of the housing with the sensor elements. This significantly reduces the cost of pulse oximeter probes, since the most significant cost element in the probe, the cable and monitor connector, can be amortized over numerous uses. Furthermore, the housing containing the sensor elements is electrically configured to be generic to all pulse oximeter instruments. In this regard, the active elements and passive elements contained therein are directly connected to the probe connector without interconnection amongst themselves. Jumper leads are provided within the cable segment of the probe to electrically interconnect these elements in a manner that is appropriate for the associated pulse oximeter instrument. Therefore, only a limited number of types of cable segments need be used to interconnect the various models of pulse oximeter instruments to the sensors contained within the housing. The housing variability is solely a function of the need to interface with a particular subject and unrelated to connector and sensor element wiring variations in pulse oximeter instruments. The pulse oximeter instrument variability is accounted for in the cable segment of the probe, since it provides the monitor connector that is specific to the pulse oximeter instrument and the associated sensor element interconnection wiring that is also specific to the pulse oximeter instrument. Therefore, the cost of manufacturing the housing elements is significantly reduced since they are more of a commodity item, useable for all pulse oximeter instruments. The economic viability of this configuration is largely due to the inexpensive probe connector that is used thereon.

The probe connector must satisfy a number of fairly stringent requirements in order to be useable in this application. In particular, the probe connector must be mechanically rugged in order to withstand numerous uses in a relatively unprotected environment. Furthermore, the probe connector must be mechanically simple and yet contain a latching mechanism to prevent accidental disconnection of the two sensor connector halves. The electrical contacts contained in the probe connector must also be simple in construction in order to minimize the cost and yet provide a low resistance, electrically continuous interconnection of the sensor elements to the pulse oximeter instrument. Any noise that is introduced into the signals produced by the probe's sensor elements significantly impairs the functioning of the pulse oximeter system. The conductors in both halves of the probe connector must therefore be precisely aligned with each other in order to provide good electrical contact therebetween when the probe connector halves are latched together.

In order to satisfy these diverse requirements, geometrically matching elements are used in the two connector halves to mechanically align the connector halves and their respective conductors. A pin and socket electrical interconnection provides a low resistance path through the sensor connector. A spring clip is used to latch the two halves of the probe connector together.

Therefore, the use of this inexpensive yet efficient probe connector arrangement enables the creation of universal housing configurations which are physically and electrically customized to the pulse oximeter instrument of choice by means of a cable segment of the probe which provides a monitor connector specific to the desired pulse oximeter instrument as well as the electrical interconnection of the sensor elements necessary for the universal housing to be compatible with the particular pulse oximeter instrument.

DETAILED DESCRIPTION

Figure 1:
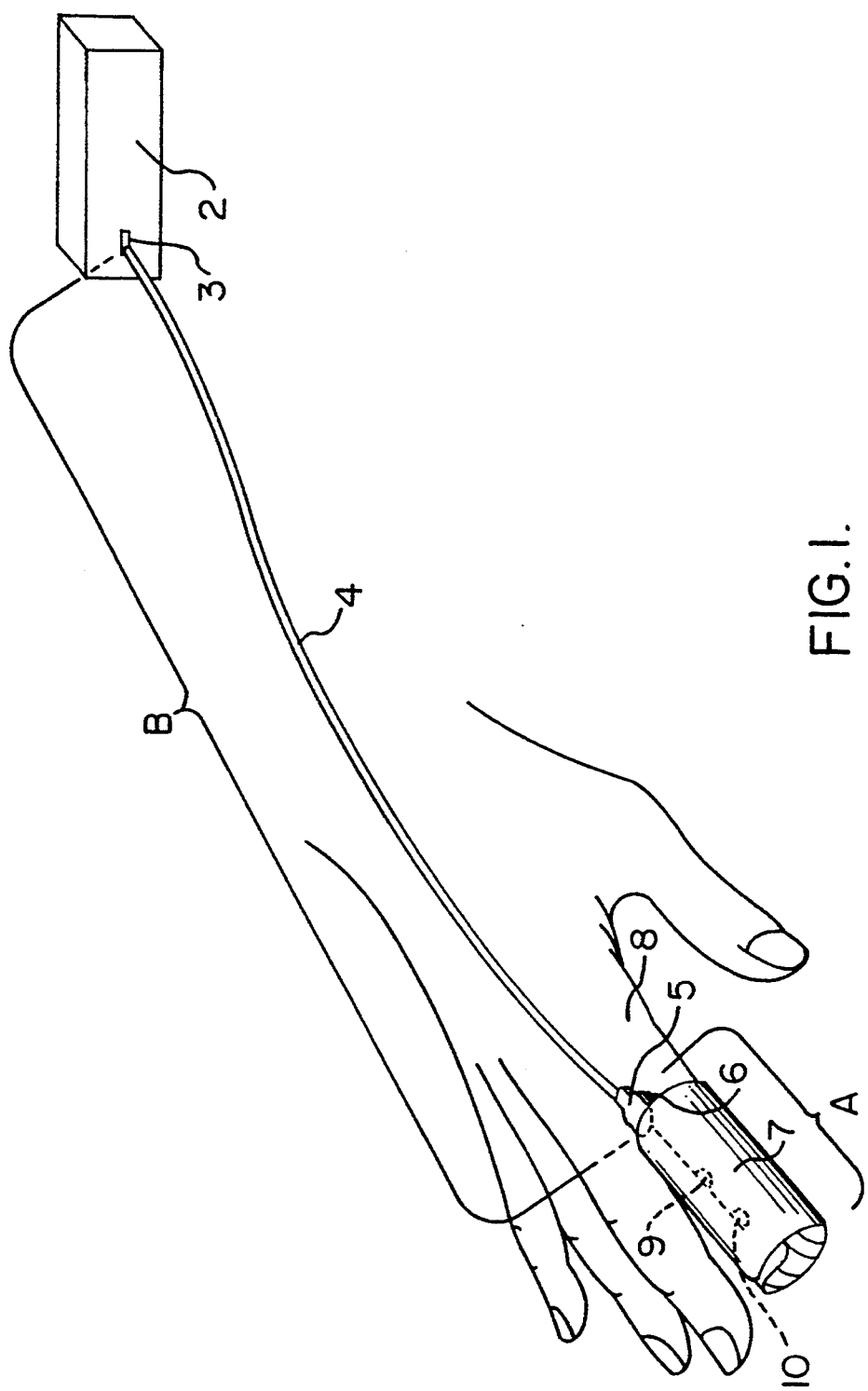
FIG. 1 illustrates, in block diagram form, the overall architecture of the pulse oximeter probe of the present invention.

FIG. 1 illustrates in block diagram form the overall system architecture of the universal pulse oximeter probe 1 of the present invention. A pulse oximeter instrument 2 is a well known device used extensively in critical care areas or hospitals to monitor a subject's arterial percentage oxygen saturation ($SpO_2$) and pulse rate (PR). The pulse oximeter instrument 2 performs these measurements by recording the absorption of light in perfused tissue at two or more wavelengths of light. The pulse oximeter instrument 2 compares the time variant and time invariant portions of the light absorption signal at the two wavelengths of light and uses this data in a well known empirical relationship to compute both the pulse rate and arterial percentage oxygen saturation.

In order to perform the measurements on the subject, the pulse oximeter system includes a probe 1 which is releasably attached to the subject 8. In a typical application, the probe 1 is releasably affixed to a subject's finger 8 or other arterial rich member of the body. The methods of releasably attaching the probe to the subject are well known in this technology and consist of mechanical clips, adhesively backed webs, and velcro webs of numerous configurations and dimensions. The probe 1 therefore includes at the distal end thereof a housing 7 that carries the sensor elements 9, 10 and the means of releasably attaching the probe to the subject.

A typical configuration of sensor elements 9, 10 includes first and second light sources 9, each of which generates a beam of light centered about a predefined wavelength. The wavelengths of these two light sources differ and are selected to detect the desired characteristics of the arterial blood as is well known in the art. The two light sources 9 are placed in the housing 7 in a manner to project the beams of light generated into the arterial tissue 8 in order to illuminate this tissue. The housing furthermore includes a light detector 10 which is positioned to measure the amount of light transmitted through the arterial tissue 8 of the subject. Typically, the two light sources 9 are activated in sequence in order that a single wavelength of light illuminates the arterial bed at a time in order to enable the single light detector 10 to measure the absorption of that wavelength of light by the arterial tissue 8. The light sources 9 are driven by pulse signals produced by the pulse oximeter instrument 2 and applied thereto via a probe connector 3 which serves to mechanically and electrically interconnect the probe 1 with connector 2a on the pulse oximeter instrument 2. A cable 4 containing a plurality of conductors is used to hard wire the light sources 9 and light detector 10 to the monitor connector 3 which plugs into connector 2a of the pulse oximeter instrument 2. The various pulse oximeter instruments 2 electrically interconnect the light sources 9, and light detector 10 in a variety of ways in order to perform the required measurements. In the prior art, each probe 1 is manufactured to be specific to a single model of pulse oximeter instrument 2 and also must be manufactured to be application specific as a function of the body part 8 to which it is attached and the nature of the subject: adult, child, infant. Therefore, the variability of subject is complicated further by the additional variable of pulse oximeter specific wiring required. These factors all contribute to the cost of the pulse oximeter probes since the probes are disposable and the greater the number of models required, the greater the cost to manufacture since there is a reduction in commonality of usage. Furthermore, the cable 4 and monitor connector 3 end of the probe represents a significant manufacturing cost that is absorbed by the subject in the single use of the probe 1.

Universal Pulse Oximeter Probe Architecture

In order to reduce the cost of probes in pulse oximeter systems, the universal probe 1 of the present invention makes use of an inexpensive probe connector 5, 6 to separate the truly disposable housing 7 and sensor element segment A of the probe 1 from the expensive and reusable cable/connecter segment B of the probe 1. By dividing the probe 1 into two sections A, B, the cost of the cable/connector segment B of the probe 1 can be amortized over numerous uses, thereby reducing the cost to the subject. Furthermore, the pulse oximeter instrument specific wiring can be implemented in the reusable portion B of the probe 1, to enable the housing segment A of the probe 1 to be of a universal configuration applicable to all pulse oximeter instruments 2 and having only a single degree of freedom: the application to a specific body part or class of patients.

Figure 2:
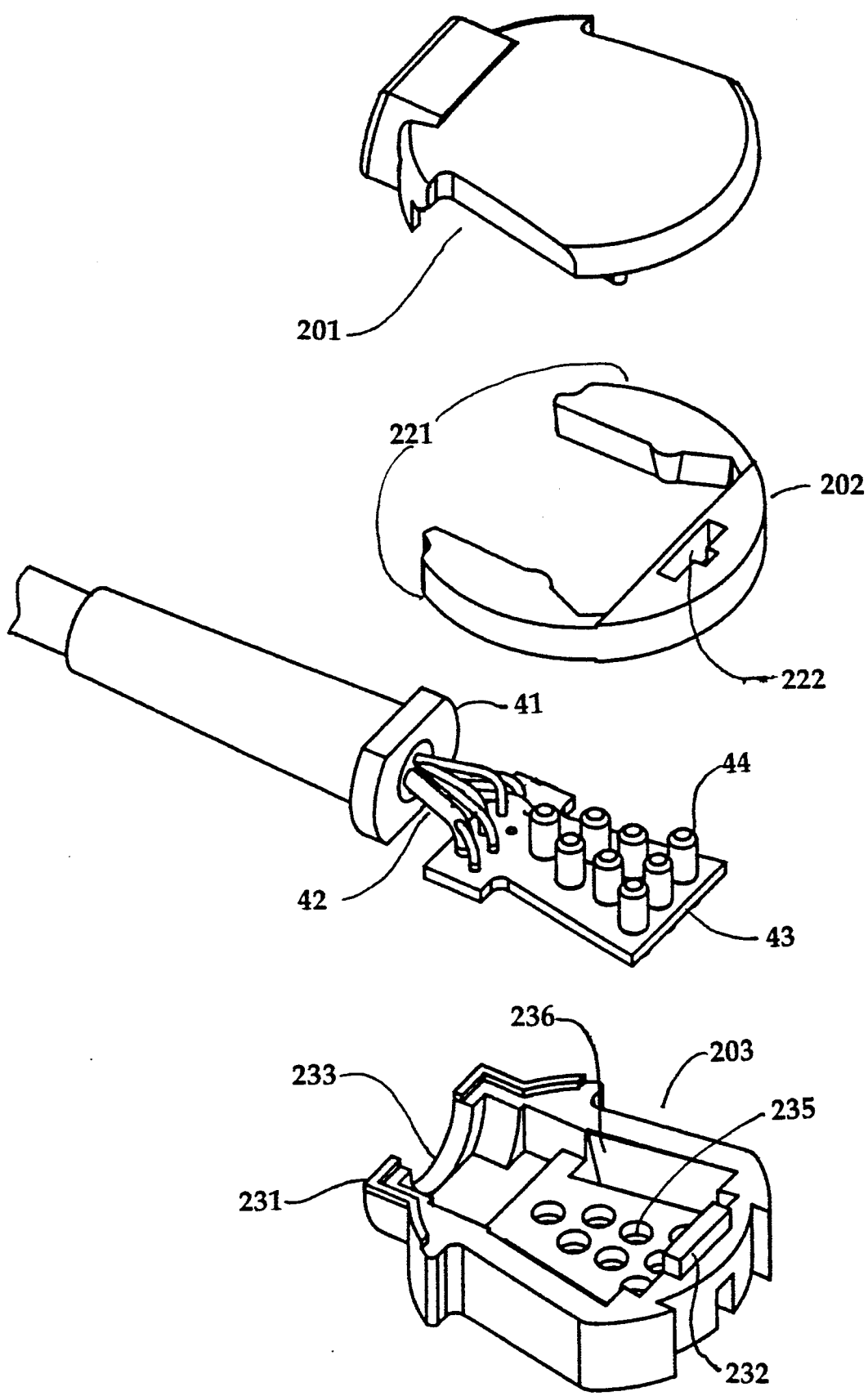
FIG. 2 illustrates an exploded view of the cable half of the probe connector.
Figure 3:
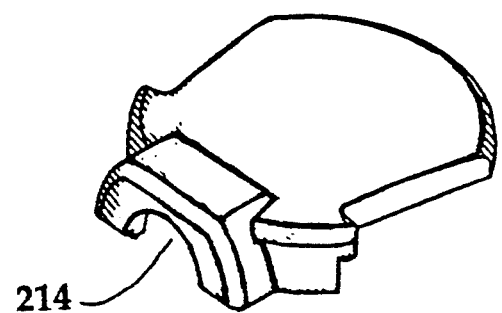
FIGS. 3 and 4 illustrate isometric views of the top and bottom of the cap of the cable half of the probe connector, respectively.
Figure 4:
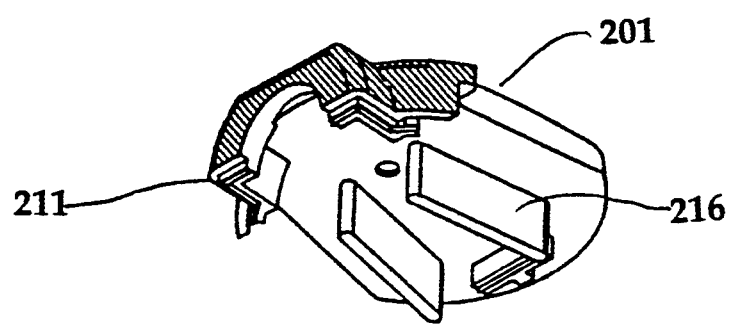
Figure 5:
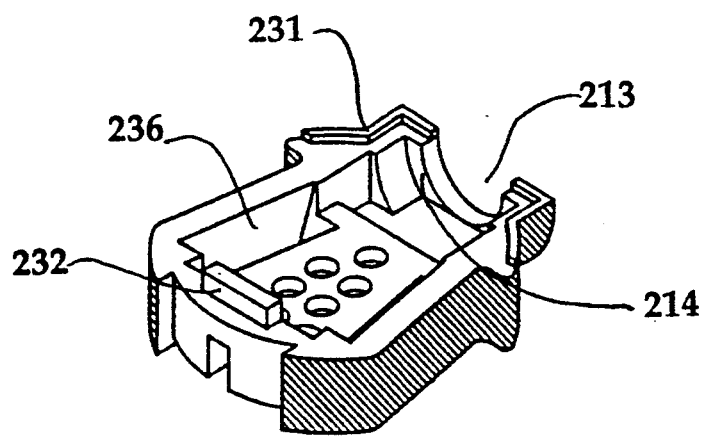
FIGS. 5 and 6 illustrate isometric views of the top and bottom of the base of the cable half of the probe connector, respectively.
Figure 6:
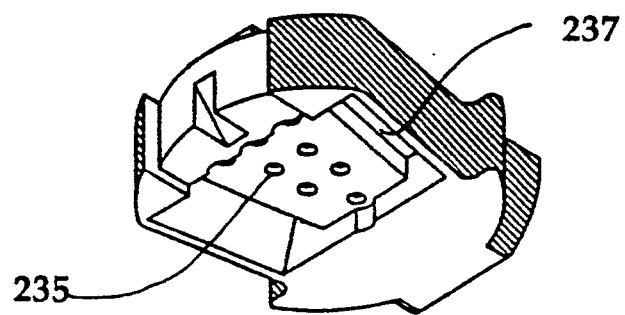
Figure 7:
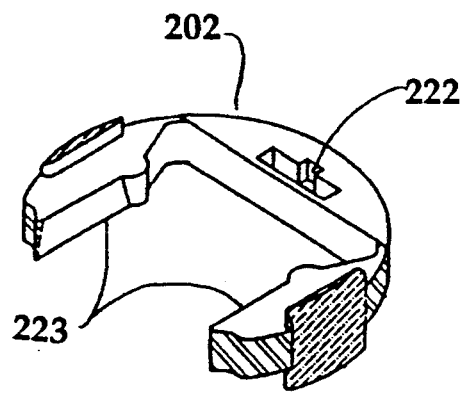
FIGS. 7 and 8 illustrate isometric views of the top and bottom of the spring clip of the cable half of the probe connector, respectively.
Figure 8:
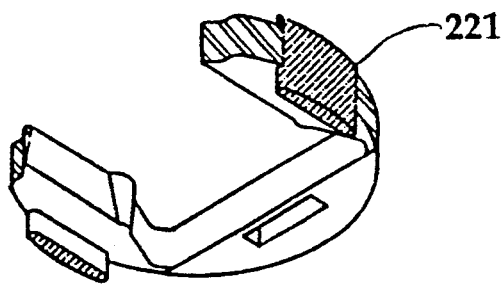
Figure 9:
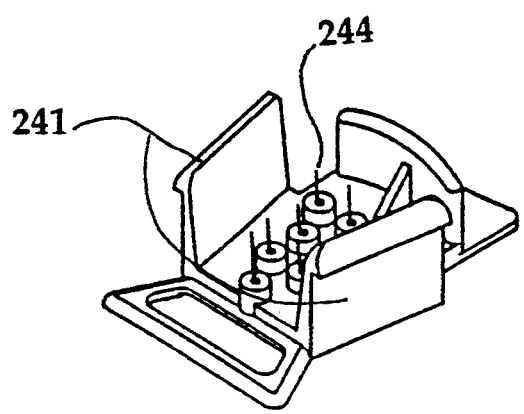
FIGS. 9 and 10 illustrate isometric views of the top and bottom of the of the housing half of the probe connector, respectively.
Figure 10:
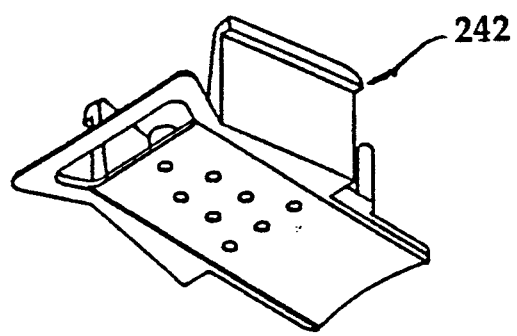

The universal pulse oximeter probe 1 is illustrated in block diagram form in FIG. 1 and FIG. 2 illustrates an exploded view of the probe connector 5, 6 that is used to segment the universal pulse oximeter probe 1 into two segments A, B. In the illustration of FIG. 1, the pulse oximeter instrument 2 is connected via a connector 2a to monitor connector 3 of cable 4 in conventional fashion in order to electrically and mechanically interconnect the probe 1 to the circuitry of the pulse oximeter instrument 2. One end of the cable 4 is connected to a probe connector 5, 6 which consists of a plurality of elements illustrated in exploded view in FIG. 2.

Cable Half of Probe Connector

The cable half 5 of the probe connector 5, 6, as also illustrated in greater detail in FIGS. 3-8, consists of a base 203, a cap 201, and a spring clip 202 interposed therebetween. The base 203 includes a shoulder 231 into which corresponding edge 211 on the cap 201 seats to interlock and position the various pieces of the connector 5. The spring clip 202 is horseshoe shaped and includes at least one notch 222 therein which notch 222 mates with the projection 212 of the cap 201 and projection 232 on base 203 in order to position the spring clip 202 in the proper orientation in the cable half 5 of the probe connector 5, 6. To mechanically assemble the cable half 5 of the probe connector 5, 6 the spring clip 202 is positioned on the base 203 and the cap 201 placed on top of the spring clip 202 such that the projection 212 of the cap 201 and projection 232 of base 203 both fit through the notch 222 in the spring clip 202. The shoulder 231 of base 203 and mating edge 211 of cap 201 are then staked or ultrasonically welded in place in order to form a unitary locked structure. Projections 216 on cap 201 align with the edges of keystone shaped aperture 236 to precisely position cap 201 with respect to base 203. The spring clip 202 is deformable such that, in the extended position, the edges 221 of the spring clip 202 extend beyond the periphery of the cap 201 and the base 203. When the spring clip 202 is compressed by a user applying force to the clip edges 221, the edges 221 are recessed such that they are flush with the periphery of the cap 201 and the base 203.

Both the cap 201 and the base 203 include a channel 213, 233 that receives the cable 4 as well as shoulder 214, 234, respectively, that engage cable strain relief 41 to prevent the withdrawal of cable 4 from cable half 5 of probe connector 5, 6 when it is assembled. The conductors 42 of cable 4 are terminated in a preformed PC board 43 on which is mounted, in a predetermined pattern, a plurality of sockets 44. The shape of PC board 43 mates with corresponding recesses in cap 201 and base 203 of cable half 5 of probe connector 5, 6 to retain PC board 43 in a predetermined position within cable half 5 of probe connector 5,6. The conductors 42 are each interconnected with a corresponding one or more of sockets 44. Base 203 includes a plurality of holes 235 that correspond in pattern and location to the pattern of sockets 44 on PC board 43, such that the open end of each of sockets 44 are juxtaposed to a corresponding hole 235 in base 203.

Housing Half of Probe Connector

The housing segment 6 of the probe connector 5, 6 consists of a U-shaped molded plastic piece with the two vertical arms 241 thereof having a lip 242 thereon for engagement of the cable half 5 of probe connector 5, 6. Thus, when the two halves of probe connector 5, 6 are placed together, the U-shaped arms 241 of the housing half 6 of probe connector 5, 6 pass through two corresponding openings 237 in the base 203 of the cable half 5 of the probe connector 5, 6 and are deformed inwardly toward each other by the force applied by the user to join the two probe connector halves 5, 6. The plastic is elastically deformable such that the two arms 241 of the housing connector 6 flex inwardly until they pass through the base 203 of the cable half 5 of probe connector 5, 6 whereupon they expand outward with the lip 242 of the arms 241 resting on the top side of the base 203 of the cable half 5 of probe connector 5, 6 to form a mechanically secure joining of the two sensor connector halves 5, 6. The spring clip 202 in the cable half 5 of probe connector 5, 6 is deformable inwardly by the user applying pressure to the two edges 222 thereof that extend beyond the periphery of the cap 201 and the base 203 of the cable half 5 of probe connector 5, 6. The deformation of the spring clip 202 causes the inside edges 223 of the spring clip to engage the arms 241 of the housing half 6 of probe connector 5, 6, causing deformation thereof such that the lip 242 of the arms 241 of the housing half 6 of probe connector 5, 6 are pressed inward to clear the inner edge of the opening 233 in the base 203 of the cable half 5 of probe connector 5, 6, enabling the user to separate the two halves of probe connector 5, 6. This probe connector 5, 6 is a simple configuration that requires little manufacturing and yet provides a fairly secure mechanical interconnection of the cable B and housing A segments of the probe 1.

The conductors in the housing end 6 of probe connector 5, 6 are similarly terminated in a like number of pins 244, also in a substantially triangular pattern, to enable the mechanical alignment of the pins 244 to provide electrical continuity between the two halves of probe connector 5, 6 when interconnected. The housing segment 6 of probe connector 5, 6 consists of a U-shaped molded plastic piece with the two vertical arms 241 thereof each having a lip 242 thereon for engagement of the cable half 5 of the probe connector 5, 6. In addition, a third projection 243 is provided to function as an alignment projection 243 to guide the two halves 5,6 of probe connector 5,6 together. The two vertical arms 241 and the alignment projection 243 form a three-point guidance system that contacts corresponding openings (for vertical arms 241) and an outer edge (for alignment projection) of the cable half 5 of probe connector 5, 6 to automatically align the pins 244 of the housing half 6 with the corresponding sockets 245 of the cable half 5 of probe connector 5, 6. This three-point guidance system precisely aligns the two halves of probe connector 5, 6 together in a simple manner. The two vertical arms 241 and the alignment projection 243 are arranged to substantially encircle pins 244 to thereby protect them from damage.

A significant concern in the sensor connector system described above is the mechanical stability and electrically conductivity of probe connector 5, 6. In order to provide mechanical stability, the pin and socket form of connector design is used in order to precisely align the two halves of probe connector 5, 6. The pin 6 and socket 5 mechanical configuration are a matter of design choice and the opening 233 in the base 203 of the cable half 5 of probe connector is a keystone shape to receive a corresponding shaped pin from the housing half 6 of probe connector 5, 6. It is obvious that other geometric orientations of the elements are possible and the shapes in the preferred embodiment are simply illustrative of the concept of the invention.

Housing Sensor Wiring

Figure 11:
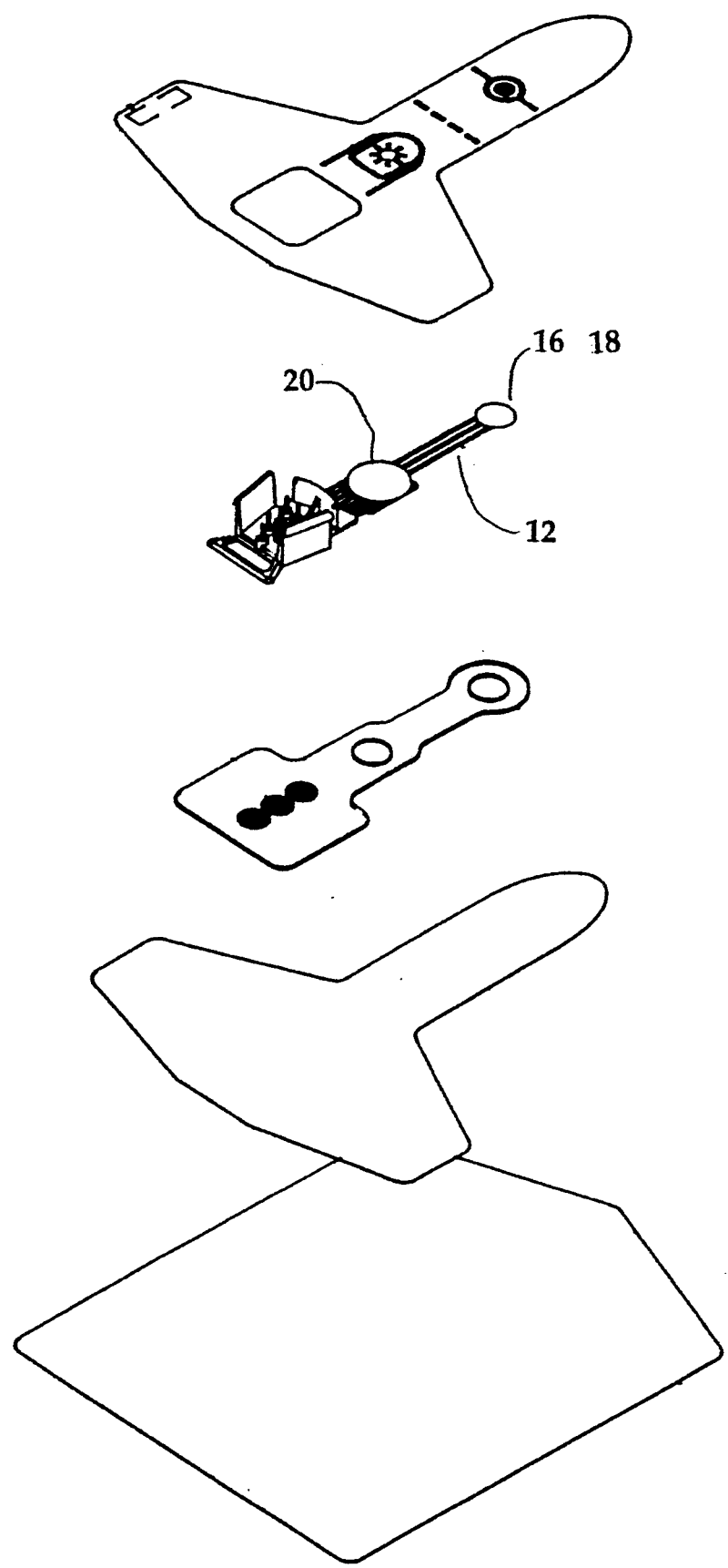
FIG. 11 illustrates details of the lead frame and housing construction.

FIG. 11 illustrates the electrical and mechanical interconnection of sensor elements 16, 18, 20, 34 in the housing 7. An integrated lead frame 12 is used to provide electrical interconnection, mechanical orientation of components, and a means for attachment of sensors 16, 18, 20 to perfused tissue. In a preferred embodiment, the lead frame 12 is made from 0.1 mm to 0.3 mm thick steel or copper sheet and eight leads 13-1 to 13-8 are formed in the lead frame 12 by stamping or chemical machining. A plastic probe connector half 6 is placed near one end of the lead frame 12 and is formed by insert molding, or attached to lead frame 12 by heat staking, ultrasonic welding or adhesive bonding. Red and infrared light emitting diodes 16, 18 ("LEDs"), a photodiode 20 and any other elements 34 (if any) are attached directly to the leads of lead frame 12. In a preferred embodiment, the attachment is made with silver filled epoxy and electrical connectors are made with gold ball or wedge bonding. Light emitting diodes 16, 18 and photodiode 20 are subsequently encapsulated in plastic lenses 22 by transfer molding or casting. The assembly is subsequently sealed in an envelope of thin, transparent plastic film (not shown) to provide electrical insulation. The insulating film may or may not be coated with pressure sensitive adhesive and it may or may not be have opaque sections between transparent windows. The electrical connector formed by the lead frame 12 and connector half 6 mates with a connector half 5 on the cable segment B of the probe 1. The device to which the pulse oximetry sensor 1 of the present invention is connected is a pulse oximeter instrument 2, such as those manufactured by Ohmeda (a division of the BOC Healthcare Group, Inc.) of Louisville, Colo. under the designation 3740.

The lead frame 12 deforms plastically as it is bent to conform to the subject's tissue, such as a finger tip 8, so that it accurately retains its shape after it is applied to the finger tip 8. The material and thickness of the lead frame 12 can be chosen to optimize this behavior. The probe 1 can be further retained in place on the finger tip 8 by pressure sensitive adhesives or bandages so that it does not tend to spring open. The low mass and thin construction of the integrated lead frame 12 act to diminish the sensor's (16, 18, 20) susceptibility to motion induced artifact, thereby enabling the lead frame 12 to be used with a wide variety of probe designs.

Sensor Interconnection

The probe illustrated in FIG. 1 can include any number of conductors. In the embodiment shown in FIG. 1, eight leads are shown, while other embodiments can include only six or seven leads. As was noted above, the electrical configuration the sensor 16, 18, 20 and other elements 34 within the housing 7 is a function of the pulse oximeter instrument 2 to which the probe 1 is connected. In order to provide a generic housing segment 7 of the probe 1, the leads 100 of the various devices 16, 18, 20, 34 contained therein are directly connected to corresponding conductors in the housing half 6 of the sensor connector without interconnection therebetween. Thus, two leads of lead frame 12 interconnect the light detector 20 while four leads interconnect the pair of light sources 16, 18 and the final two leads of lead frame 12 interconnect the optional other elements 34. The eight leads therefore provide electrical access to each terminal of every device contained within the housing 7. The resultant housing 7 is therefore generic to all pulse oximeter instruments 2 since there is no electrical interconnection of the elements 16, 18, 20, 34 contained therein and the cable segment B of the probe is used to provide the electrical interconnection to satisfy the requirements of the corresponding pulse oximeter instrument 2. The cable segment B of the probe 1 therefore physically and electrically interconnects the conductors of the cable 4 to the pulse oximeter instrument 2 as well as electrically interconnects the various conductors from the housing 7 to wire the sensor 16, 18, 20 and other 34 elements contained therein to electrically mate with the corresponding connector 2a of pulse oximeter instrument 2.

Therefore, the use of the inexpensive probe connector 5, 6 provides a means for converting the expensive probes of the prior art into an inexpensive probe system I that comprises a reusable cable segment B and an inexpensive disposable universal housing segment A that can be used with all pulse oximeter instruments 2 due to the electrical programming capability of the cable segment B of the probe 1.

While a specific embodiment of this invention has been disclosed, it is expected that those skilled in the art can and will design alternate embodiments of this invention that fall within the scope of the appended claims.

We claim:

1. A connector for electrically connecting first and second sets of conductors to exchange signals therebetween, comprising:
   first connector segment, having a top side, a bottom side and at least one edge, comprising:
   a plurality of sockets located on said bottom side of said first connector segment and configured in a predetermined pattern, each of said plurality of sockets being connected to a one of said first set of conductors,
   first and second apertures in said bottom side of said first connector segment, second connector segment, having a top side and a bottom side, comprising:
   a like plurality of pins located on said top side of said second connector segment and configured in said predetermined pattern, each of said plurality of pins being connected to a one of said second set of conductors,
   first projection located along a first side of said predetermined pattern of pins, and mating with said first aperture in said bottom side of aid first connector segment,
   second projection located along a second side of said predetermined pattern of pins, and mating with said second aperture in said bottom side of said first connector segment, and
   alignment projection located on said top side of said second connector segment engagable with said edge on said first connector segment and cooperatively operative with said first and second projections for positioning said first and second connector segments to align said plurality of pins with said plurality of sockets, said first and second projections in combination with said alignment projection forming a substantially U-shaped configuration of elements to partially encircle said plurality of pins that project from said top side of said second connector segment.

2. The apparatus of claim 1 wherein said at least one projection comprises:
   tab means engagable with said aperture to lock said first connector segment to said second connector segment when said first and second connector segments are interconnected.

3. The apparatus of claim 2 further comprising:
   spring clip means engagable with said tab means for disengaging said tab means from said aperture when said spring clip means is operated by a user.

4. The apparatus of claim 1 wherein said bottom side of said first connector section and said top of said second connector section are each shaped to be geometrically mating elements.

5. The apparatus of claim 1
wherein said first and second projections in combination with said predetermined pattern of pins form a U-shaped connector.

6. The apparatus of claim 5 wherein said aperture comprises:
first opening formed in said bottom of said first housing segment and located along a first side of said predetermined pattern of sockets;
second opening formed in said bottom of said first housing segment and located along a second side of said predetermined pattern of sockets; and
wherein said first opening and said second opening are oriented to receive said first projection and said second projection.

7. The apparatus of claim 6 wherein said second housing segment further comprises:
first tab means formed on an end of said first projection located distal from said predetermined pattern of pins;
second tab means formed on an end of said second projection located distal from said predetermined pattern of pins; and
wherein said first tab means and said second tab means are engagable with said first opening and said second opening, respectively, to lock said first connector segment to said second connector segment.

8. The apparatus of claim 7 further comprising:
user activated spring means activatable to release said tab element from said opening when said first housing segment is interconnected with said second housing segment.

9. The apparatus of claim 1 wherein said predetermined pattern of pins is substantially trapezoid in shape, said first and second projections being aligned substantially juxtaposed to and along equal opposite sides of said trapezoid shape pattern of pins, said alignment projection being aligned substantially juxtaposed to and along a remaining side of said trapezoid shape pattern of pins.

10. The apparatus of claim 1 wherein said first and second projections extend at least of height above said top side of said second connector segment greater than said pins.

11. The apparatus of claim 1 wherein said alignment projection extends at least of height above said top side of said second connector segment greater than said pins.

12. The apparatus of claim 3 wherein said spring clip means substantially encircles said first and second projections and said alignment projection and is movable to engage only said first and second projections to release said tab means.

* * * * *